United States Patent
Ishikawa et al.

[11] Patent Number: 6,024,088
[45] Date of Patent: Feb. 15, 2000

[54] BREATH SYNCHRONIZATION CONTROL UNIT FOR GAS FEEDER

[75] Inventors: Shiro Ishikawa; Masao Takahashi, both of Isesaki; Masayoshi Kanazawa; Eitaro Hayakawa, both of Tokyo; Yuki Murayama; Takashi Sato, both of Chiba, all of Japan

[73] Assignees: Koike Medical Co., Ltd., Sumitomo Medical Mining Co., Ltd., Tokyo; Gunma Koike Co. Ltd., Gunma, both of Japan

[21] Appl. No.: 08/793,615

[22] PCT Filed: Jul. 12, 1996

[86] PCT No.: PCT/JP96/01947

§ 371 Date: Mar. 12, 1997

§ 102(e) Date: Mar. 12, 1997

[87] PCT Pub. No.: WO97/02858

PCT Pub. Date: Jan. 30, 1997

[30] Foreign Application Priority Data

Jul. 12, 1995 [JP] Japan .................................. 7-175702

[51] Int. Cl.[7] .................................................. A61M 16/00
[52] U.S. Cl. ................................ 128/204.21; 128/204.23
[58] Field of Search ........................ 128/204.21, 204.23, 128/204.26, 722; 600/535

[56] References Cited

U.S. PATENT DOCUMENTS

| | | | |
|---|---|---|---|
| 4,784,130 | 11/1988 | Kenyon et al. | 128/204.23 |
| 4,827,922 | 5/1989 | Champain et al. | 128/204.21 |
| 5,074,299 | 12/1991 | Dietz | 128/204.23 |
| 5,134,886 | 8/1992 | Ball | 128/204.23 |
| 5,367,292 | 11/1994 | Szoke et al. | 128/722 |

*Primary Examiner*—Aaron J. Lewis
*Attorney, Agent, or Firm*—Townsend & Banta

[57] ABSTRACT

A breath-synchronization control unit for a gas feeder, capable of reliably detecting inhalation and supplying a gas, which serves to control the gas feeder to supply a gas from a gas source in synchronization with the breath. Such a unit comprises a breath detector having a substrate on which a plate-like piezoelectric element is supported at one end or both ends thereof, in a container formed with an outside air vent at a position opposed to a surface of the piezoelectric element and a breath vent hole extending in the direction parallel to the surface of the piezoelectric element to detect a change in pressure of air introduced through the respective vent holes and generate an electric signal in response to the detection; a gas passage coupled to the breath vent hole formed on the container such that the inhalation and the expiration act thereupon wherein the gas is permitted to be supplied therethrough upon inhalation; an electromagnetic valve disposed on the gas passage and having a normally closed port coupled to the gas source; and a control section for actuating the electromagnetic valve to establish communication between the gas source and the gas passage for a predetermined period of time which, based on electric signals generated from the breath detector, simultaneously cuts off communication between the breath detector and the gas passage when inhalation is detected.

2 Claims, 6 Drawing Sheets

BREATH SYNCHRONIZATION CONTROL UNIT FOR GAS FEEDER

TECHNICAL FIELD

The present invention relates to a breath synchronization control unit for use in a gas feeder, which is capable of supplying a gas (an oxygen gas) in synchronization with the breath.

BACKGROUND ART

When patients suffering from a chronic respiratory decease are caused to inhale an oxygen gas, it is unsuitable to supply the oxygen gas continuously, because some resistance against the expiration of the patient is generated due to the pressure of oxygen gas supplied during the expiration, and there is a loss of oxygen gas not inhaled by the patient. For this reason, there has been developed such a technique that an oxygen gas is permitted to be supplied only upon the inhalation by detecting the breath timing of the patient.

For example, Japanese Patent Application Laid-open No. 270170/87 discloses the technique in which a breath sensor containing a pyroelectric element is disposed in a nose cannula attached to a nose of the patient to control the supply of oxygen gas in response to electric signals from the breath sensor. In this technique, the change in temperature in the nose cannula caused by the breath of the patient is detected by the pyroelectric element to generate corresponding electric signals. When the level of the electric signals exceeds a predetermined trigger level for the inhalation, the electromagnetic valve is opened to supply oxygen gas to the nose cannula. Also, when the level of the electric signal exceeds another trigger level for the Expiration, the electromagnetic valve is closed to interrupt the supply of oxygen gas.

In addition, Japanese Patent Application Laid-open No. 143082/88 discloses the technique further developed from the afore-mentioned technique, in which at least one electromagnetic valve is provided in a nose cannula to control the supply of oxygen gas by opening and closing operations thereof in response to electric signals generated from a breath sensor. In this technique, the supply of oxygen gas can be carried out with an excellent responsibility to the breath and the concentration of oxygen gas supplied can be kept stable.

Further, there is also known such an arrangement that a diaphragm-type high-sensitive pressure sensor is used as a sensor for detecting the breath, and a nose cannula and an oxygen source are coupled to each other through a three-way valve. When the pressure sensor detects the inhalation transmitted through the nose cannula, electric signals are generated to control the three-way valve. This arrangement enables the oxygen gas to be supplied through the nose cannula for a predetermined period of time.

On the other hand, there has been proposed an air pressure change detector comprising a strip-like piezoelectric element supported at one end thereof on a substrate which is accommodated in container having a vent hole at a position opposed to the piezoelectric element (Japanese Patent Laid-open No. 208827/92). In this air pressure change detector, an outside air is introduced into an interior of the container through the vent hole. When the pressure change in the outside air occurs, the pressure change is propagated to air in the container to cause the air to vibrate. The vibration of the air in turn induces the vibration of the piezoelectric element so that electric signals are generated therefrom, thereby enabling the detection of the change in air pressure. Especially, since the piezoelectric element is supported in a cantilever-like manner, the piezoelectric element is responsive to an extremely weak and low-frequency aerial vibration. By this arrangement, the air pressure change detector can detect an extremely small change in air pressure.

In the afore-mentioned techniques disclosed in Japanese Patent Laid-open Nos. 208827/92 and 143082/88, the breath sensor constituted by the pyroelectric element is disposed in the nose cannula and exposed to the expiration to accurately detect the temperature change occurring in association with the breath. However, since the pyroelectric element shows a low resistance to humidity or moisture, there is such a risk that if the pyroelectric element is used for a long period of time, the required performance thereof is lost. In addition, if the nose cannulae, which are usually handled as disposable items, are provided thereon with the breath sensor and signal conductors for such an exclusive use, there arises a problem that they are too expensive to be handled as disposable items, or there is a risk that breakage or burnout of the signal conductors are caused in association with repeated and frequent use thereof.

In the case where the diaphragm-type high-sensitive pressure sensor is used, extremely small pressure change (for example, on the order of 0.04 Pa) can be detected. However, since the diaphragm-type high-sensitive pressure sensor has an extremely low resistance to burst pressure, there also arises a problem that the sensor is readily damaged by pressure change frequently occurring in daily use, e.g., when the nose cannula is held in the mouth.

Further, in the case where the air pressure change detector having such a construction that the piezoelectric element is supported at one end thereof on the substrate accommodated in the container, is used and the nose cannula is coupled to the vent hole formed on the container at the position opposed to the piezoelectric element, the pressure change can be detected in response to the breath without a risk that the piezoelectric element is adversely affected by humidity or moisture. However, the aerial vibrations associated with both the inhalation and the expiration act similarly upon the piezoelectric element, so that the piezoelectric element are vibrated in an approximately similar manner upon the inhalation and the expiration. Therefore, it becomes difficult to distinguish the inhalation and the expiration from each other based on electrical signals generated from the piezoelectric element. This causes a problem that the supply of oxygen gas cannot be controlled only by the electric signals generated from the piezoelectric element.

Accordingly, it is an object of the present invention to provide a breath-synchronization control unit for use in a gas feeder, which is capable of surely detecting the inhalation to supply a gas, and free from breakage or failure even upon misuse thereof frequently occurring in daily use.

DISCLOSURE OF THE INVENTION

In accordance with the present invention, there is provided a breath-synchronization control unit for a gas feeder for supplying a gas from a gas source in synchronization with the breath, which unit comprises a breath detector constituted by accommodating a substrate on which a plate-like piezoelectric element is supported at one end or both ends thereof, in a container formed with an outside air vent hole at a position opposed to a surface of the piezoelectric element and a breath vent hole extending in the direction parallel to the surface of the piezoelectric element to detect a change in pressure of air introduced through the respective vent holes and generate electric signals in response to the detection; a gas passage coupled to the breath vent hole formed on the container such that the inhalation and the expiration act thereupon and the gas is permitted to be supplied therethrough upon the inhalation; an electromagnetic valve disposed on the gas passage and having a normally closed port coupled to the gas source; and a control section for actuating the electromagnetic valve to establish a communication between the gas source and the gas passage for a predetermined period of time and simultaneously cut off a communication between the breath detector and the gas passage when the inhalation is detected based on the electric signals generated from the breath detector.

In the afore-mentioned breath-synchronization control unit for the gas feeder (hereinafter referred to merely as "synchronization control unit"), the breath detector (hereinafter referred to merely as "detector") used therein is constituted by accommodating the plate-like substrate on which the piezoelectric element is supported at one end or both ends thereof, in the container formed with the outside air vent hole at the position opposed to the surface of the piezoelectric element and the breath vent hole extending along the direction parallel with the surface of the piezoelectric element, and the detector is coupled to the gas passage upon which the expiration and the inhalation act and through which the gas is permitted to be supplied upon the inhalation. By this arrangement, when the expiration acts upon the gas passage, air in the container is permitted to flow in the direction approximately parallel with the surface of the piezoelectric element and discharged outside through the outside air vent hole. Accordingly, the piezoelectric element is caused to oscillate with a small amplitude, thereby generating the electric signals having a small amplitude.

In addition, when the inhalation acts upon the gas passage, air in the container flows toward the side of the gas passage so that outside air is introduced into the container through the outside air vent hole and acts upon the surface of the piezoelectric element in the direction approximately perpendicular thereto. For this reason, the piezoelectric element is caused to oscillate with a large amplitude, thereby generating the electric signals having a large amplitude. That is, the expiration and the inhalation can be identified respectively based on the electric signals generated.

Accordingly, it is possible to supply the gas for a predetermined period of time in synchronization with the breath, by identifying, in the control section, the expiration and the inhalation based on the electric signals generated from the detector and actuating the electromagnetic valve for the predetermined period of time to establish the communication between the gas passage and the gas source and simultaneously cut off the communication between the gas passage and the detector.

BEST MODE FOR CARRYING OUT THE INVENTION

Figure 1:
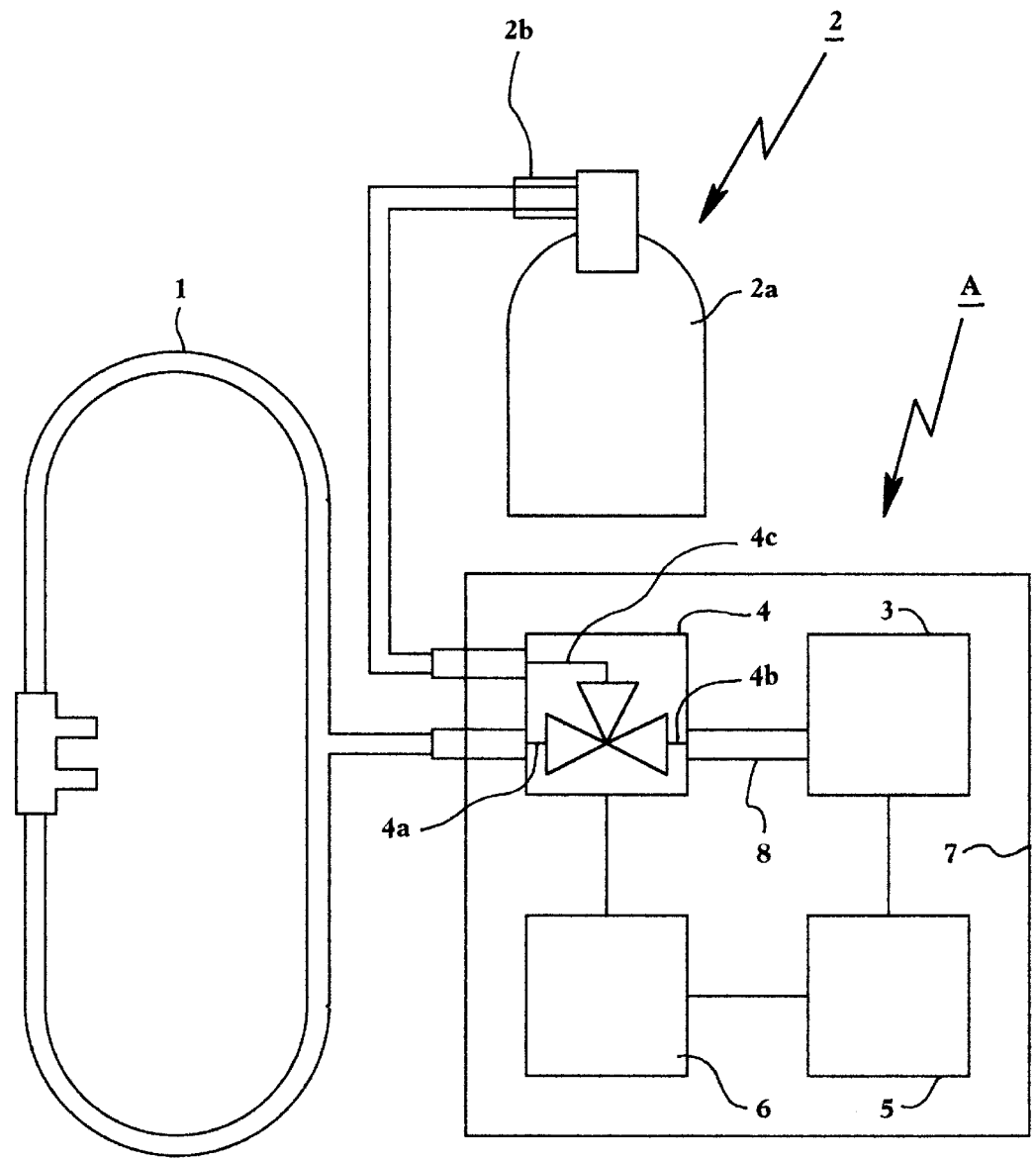
FIG. 1 is a block diagram showing an arrangement of a gas feeder to which a synchronization control device according to the present invention is applied.
Figure 2A:
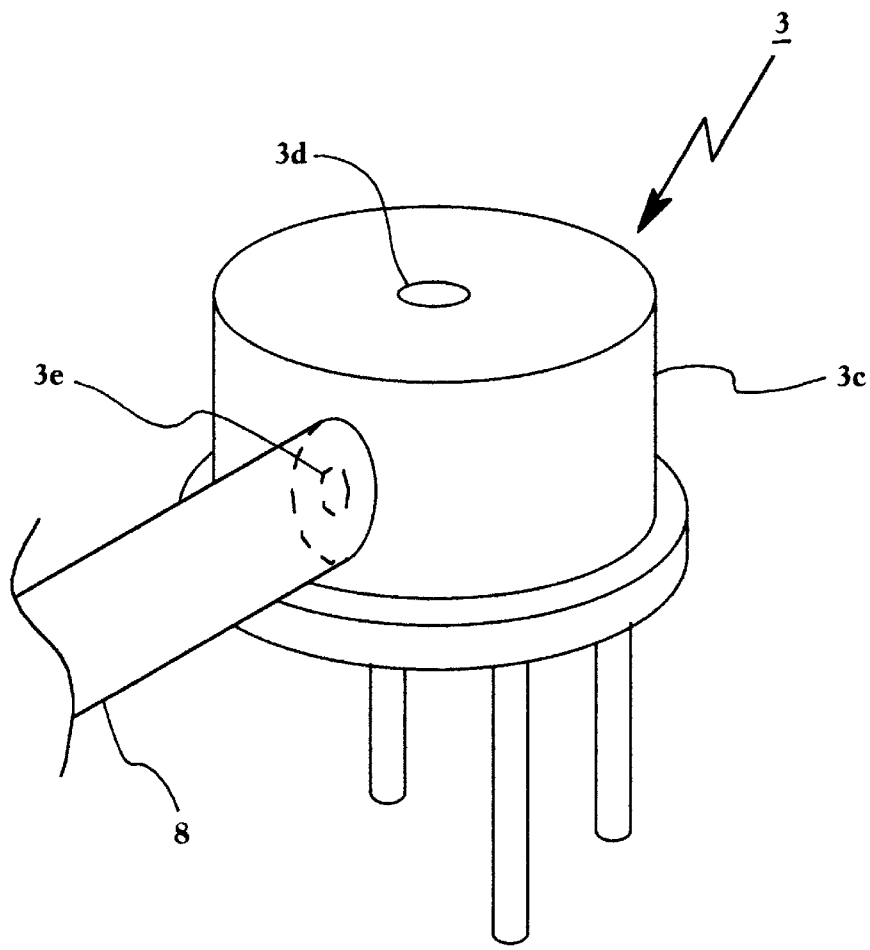
FIGS. 2(a) and 2(b) are views showing an arrangement of a detector.
Figure 2B:
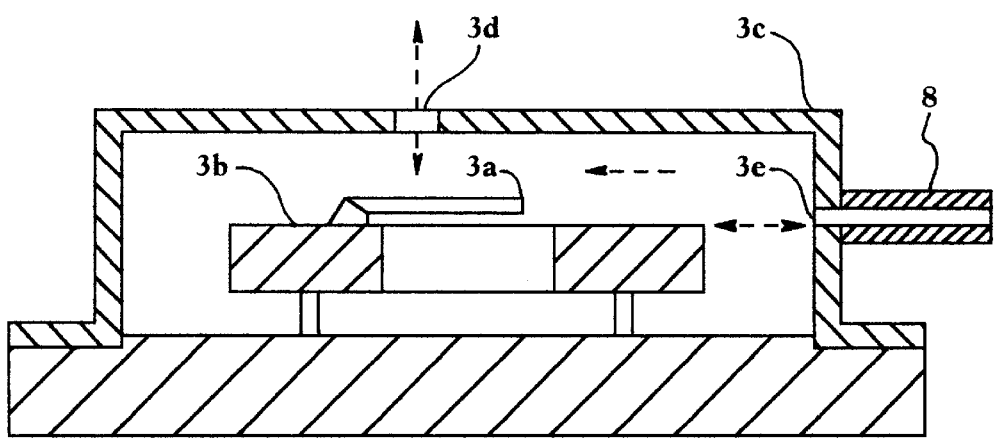
Figure 3:
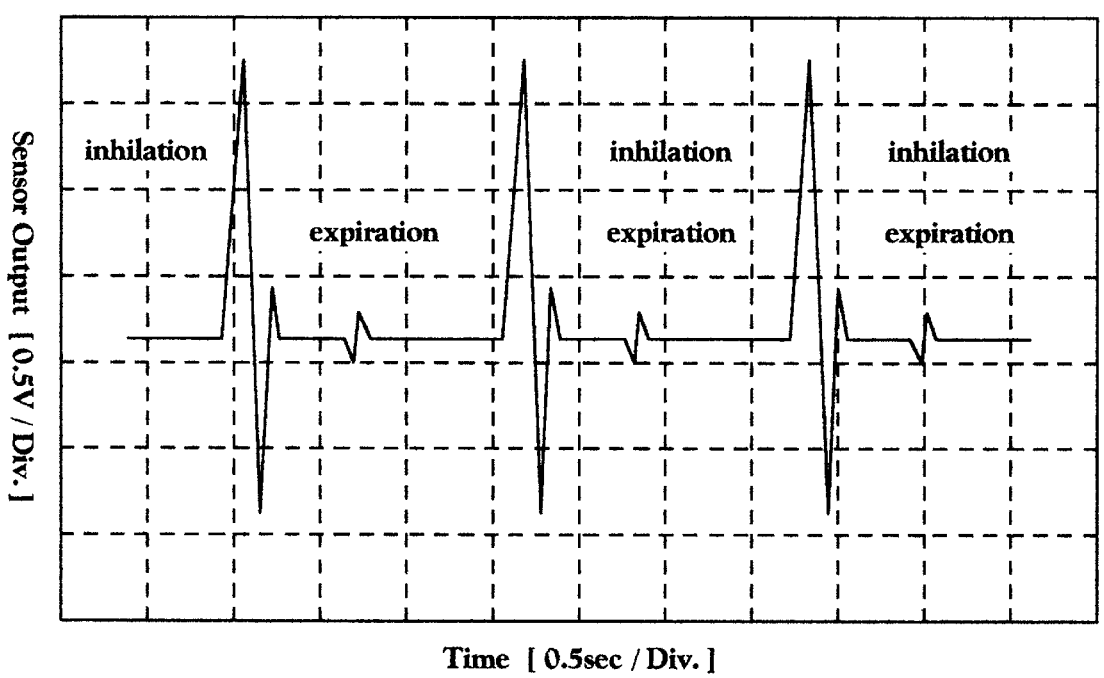
FIG. 3 is a view showing electric signals detected by the detector.
Figure 4:
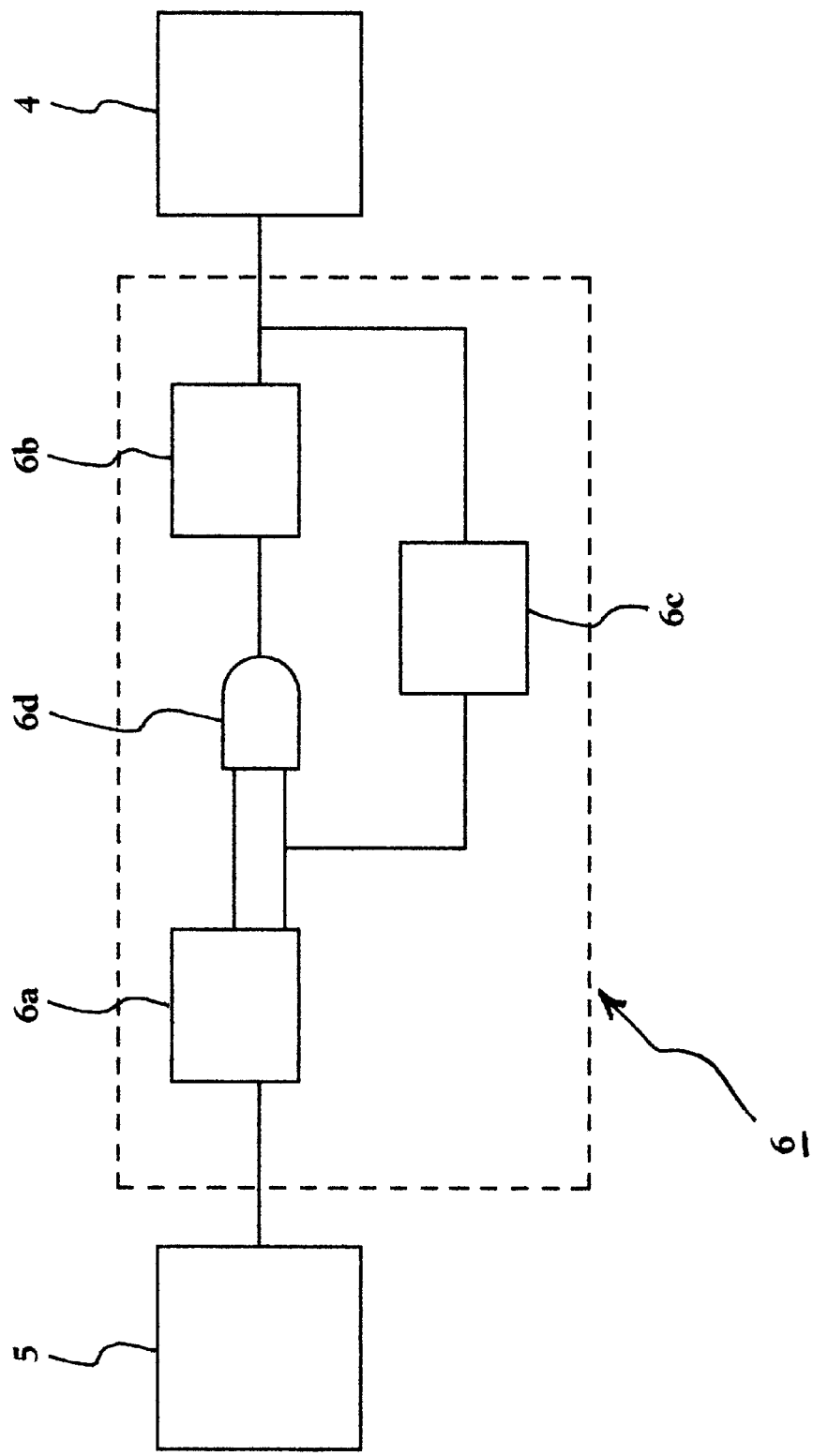
FIG. 4 is a block diagram showing an arrangement of a control circuit.
Figure 5:
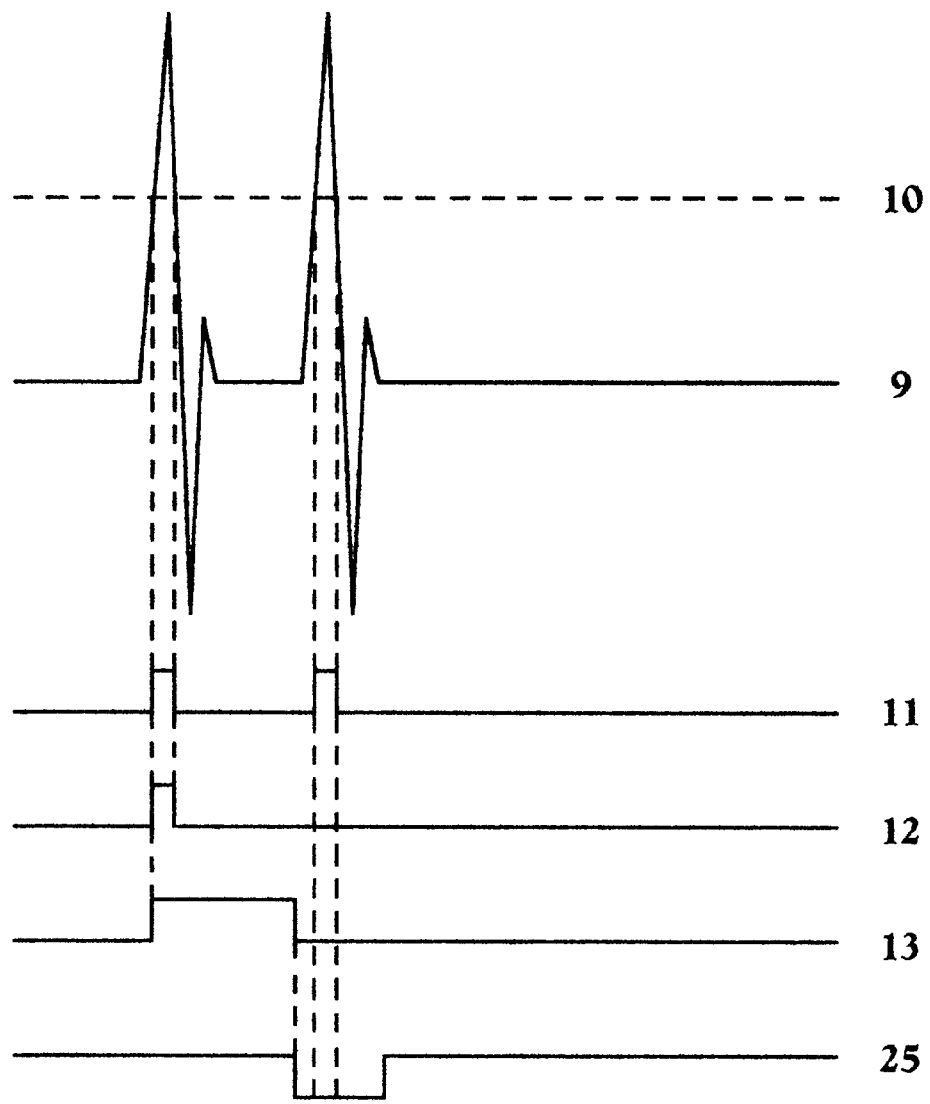
FIG. 5 is a timing chart showing operations of the control circuit.
Figure 6:
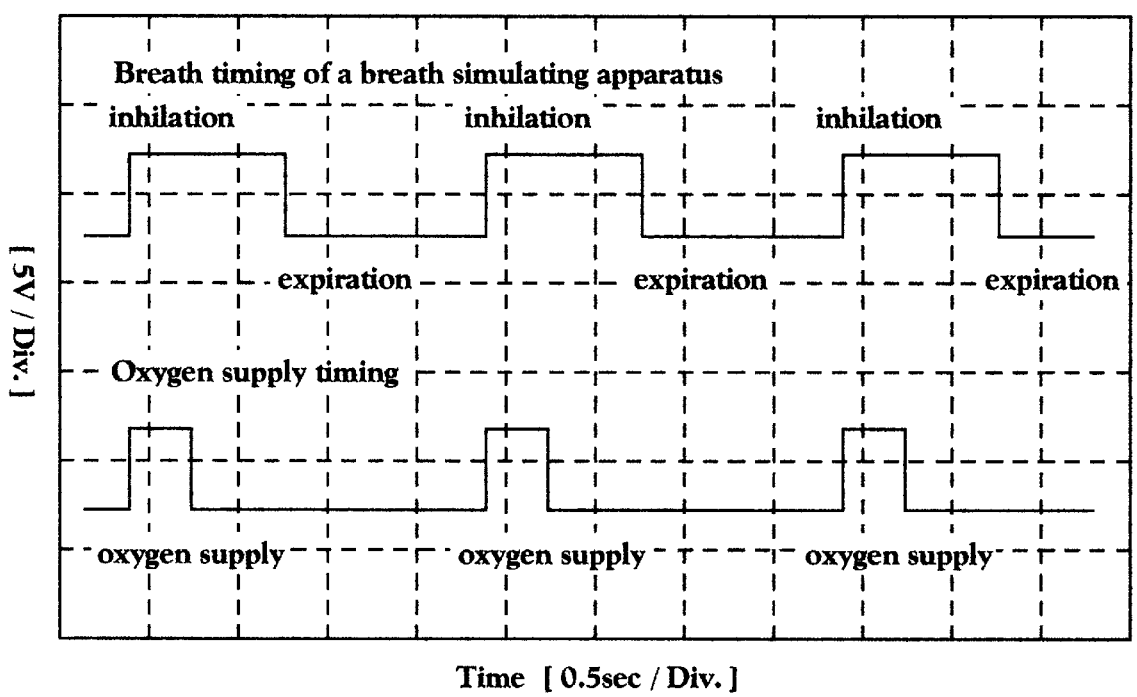
FIG. 6 is a view showing a gas supply condition when the gas feeder is applied to a breath simulating apparatus.

The gas feeder to which the afore-mentioned synchronization control unit according to the present invention is applied, is explained below by referring to the accompanying drawings, in which FIG. 1 is a block diagram showing an arrangement of the gas feeder to which the synchronization control device according to the present invention is applied; FIGS. 2(a) and 2(b) are views showing an arrangement of the detector; FIG. 3 is a view showing electric signals detected by the detector; FIG. 4 is a block diagram showing an arrangement of a control circuit; FIG. 5 is a timing chart showing operations of the control circuit; and FIG. 6 is a view showing the gas supply condition when the gas feeder according to the present invention is applied to the breath simulating apparatus.

The gas feeder shown in FIG. 1 is so constructed as to permit a patient suffering from chronic respiratory disease to inhale oxygen, and comprises a nasal cannula 1 cannulated to a nose of the patient and a gas source 2. The gas supplied from the gas source 2 is fed through a synchronization control unit A according to the present invention, so as to synchronize the feed of gas with an inhalation of the patient. Specifically, the change in pressure acting on the nasal cannula 1 as a gas passage, which is caused in response to inhalation and expiration of the patient, is detected by a detector 3 provided in the synchronization control unit A, and the gas source 2 and the nasal cannula 1 is communicated with each other by actuating in electromagnetic valve 4 upon detecting the inhalation of the patient, thereby feeding the gas in synchronization with the breath of the patient.

In the preferred embodiment of the present invention, the explanation is made as to the case where the nose cannula 1 is used as a member constituting the gas passage on which both the inhalation and the expiration of the patient act and through which a gas is permitted to be supplied upon the inhalation. However, the member constituting the gas passage is not necessarily limited to the nose cannula 1. For example, a mask covering a face of the patient and a mouth piece retainable in the mouth can also be used as the member constituting the gas passage.

Incidentally, in the preferred embodiment of the present invention, it is not required to provide a sensor for detecting the breath of the patient, in the nose cannula 1. Therefore, as the nose cannula 1, there can also be used commercially available ones which can be handled as disposable items.

As the suitable gas to be supplied to the patient, an oxygen gas, especially a medical oxygen gas is suitably used. For this reason, the gas source 2 is constituted by an oxygen bomb 2a and a controller 2b such as a pressure controller or a flow controller, which is detachably mounted on the oxygen bomb 2a. Accordingly, it is possible to supply the oxygen gas from the gas source 2 at a constant pressure or a constant flow rate.

Meanwhile, the gas to be supplied in synchronization with the breath is not necessarily limited to the oxygen gas. For example, in the case where the synchronization control unit A is applied to a diving apparatus, air can also be used as the gas. Even in such a case, the gas source 2 can be similarly constituted by the bomb 2a and the controller 2b.

The synchronization control unit A comprises the detector 3, the electromagnetic valve 4, an amplifier circuit 5 for amplifying the electric signals generated from the detector 3, and a control section 6 for actuating the electromagnetic valve 4 in response to the electric signals amplified by the amplifier circuit 5. The synchronization control unit A also has a casing 7 in which the afore-mentioned parts or members 3 to 6 are mounted at predetermined positions.

In the case where the breath of the patient is detected through the nose cannula 1, it is required that the detector 3 is capable of detecting the change in pressure on the order of 0.04 Pa. To this end, as shown in FIG. 2, the detector 3 has such a structure that a piezoelectric element 3a shaped into a thin plate is supported at one end thereof by a substrate 3b, and the substrate 3c is accommodated within a container 3c. The casing 3c is formed, on a position thereof opposite to a surface of the piezoelectric element 3a, with an outside air vent hole 3d communicating with outside air. Further, the casing 3c is formed with a breath vent hole 3e extending in parallel with the surface of the piezoelectric element 3a. The breath vent hole 3e is coupled with a tube 3 which is communicated with the nose cannula 1 through the electromagnetic valve 4.

In the afore-mentioned arrangement of the detector 3, the piezoelectric element 3a is supported only at one end thereof by the substrate 3b and therefore permitted to oscillate in response to extremely weak and low-frequency aerial vibration, thereby enabling electric signals corresponding to the aerial vibration to be generated. This arrangement makes it possible to detect the change in pressure on the order of 0.01 Pa. Incidentally, in the case where the piezoelectric element 3a is supported by the substrate 3b, it is not necessarily required that the piezoelectric element 3a is held only at one end thereof on the substrate 3b. The piezoelectric element 3a may be supported at opposite ends thereof by the substrate 3b.

When the expiration acts on the nose cannula 1 and the tube 8, air is flowed in the container 3c in the direction parallel with the surface of the piezoelectric element 3a as indicated by a dash line in FIG. 2(b) and discharged outside through the outside air vent hole 3d. As a result, the piezoelectric element 3a is prevented from oscillating with a large amplitude so that the electric signals generated also have a small amplitude.

Further, in the case where there occurs such an accident that the nose cannula 1 is held in the mouth and a relatively large pressure exerted on the nose cannula 1 is introduced into the container 3c, the air flow generated due to the pressure fluctuation does not act directly on the surface of the piezoelectric element 3a and the air can be rapidly discharged through the outside air vent hole 3d to the outside. That is, the interior of the container 3c is avoided from being exposed to drastic pressure rise and retained at the elevated pressure, so that the detector 3 is free from failure or breakage thereof.

When the inhalation acts on the nose cannula 1 and the tube 8, air in the container 3c is absorbed into the tube 8 and the outside air is introduced through the outside air vent hole 3d into the interior of the container 3c and acts upon the surface of the piezoelectric element 3a in the direction perpendicular thereto as indicated by a solid line in FIG. 2(b). As a result, the piezoelectric element 3a is caused to oscillate with a large amplitude so that the electric signals having a large amplitude is generated.

As the electromagnetic valve 4, there can be used a three-way valve. The electromagnetic valve 4 has an IN port (normally open port) 4a coupled with the nose cannula 1, an OUT port (normally open port) 4b coupled with the tube 8 communicated with the breath vent hole 3e of the detector 3, and an EX port (normally closed port) 4c coupled with the gas source 2.

Accordingly, when the electromagnetic valve 4 is inoperative, the IN port 4a and the OUT port 4b are communicated with each other and the change in pressure generated in response to the inhalation and the expiration acting upon the nose cannula 1 is introduced to the detector 3. On the other hand, when the electromagnetic valve 4 is operative, the communication between the IN port 4a and the OUT port 4b is cut off and the communication between the IN port 4a and the EX port 4c is established so that oxygen gas is supplied from the gas source 2 to the nose cannula 1.

Since the electric signals generated from the detector 3 have an extremely small amplitude, they are amplified by the amplifier circuit 5 and then transmitted to the control section 6. The amplification factor of the amplifier circuit 5 is set to 70 dB. The output of the piezoelectric element 3a constituting the detector 3 is apt to be adversely affected by an external temperature. In order to eliminate this problem, a low-frequency cutoff filter is preferably used. Further, a high-frequency cutoff filter is preferably used to eliminate the adverse affect by high-frequency noises. Furthermore, it is preferable to use a band-pass filter so as to permit signal components on the order of 0.1 Hz to 100 Hz to be amplified.

The afore-mentioned detector 3 is of a differential detection type. Therefore, the electric signals output from the detector 3 have acute peak values. In the preferred embodiment of the present invention, the electric signals output from the detector 3 are amplified by the amplifier circuit 5 at a center frequency of 30 Hz, a lower limit frequency of 7 Hz and an upper limit frequency of 100 Hz, and then supplied to the control section 6.

In FIG. 3, there is shown the electric signals which are output from the breath detector 3 and amplified by the amplifier circuit 5. As is apparently appreciated from FIG. 3, the peak values of the electric signals generated upon the inhalation are approximately four times those generated upon the expiration. Accordingly, based on the electrical signals, the inhalation and the expiration can be readily distinguished from each other.

The control section 6 has a function for controlling the electromagnetic valve 4 in such a manner that when the signal indicative of the inhalation of the patient is detected from the electric signals supplied from the amplifier circuit 5, the electromagnetic valve 4 is actuated for a predetermined period of time. The control section 6 is constituted by a comparator 6a, an output circuit 6b, a mask signal generator circuit 6c and a logic circuit 6d. This arrangement enables oxygen supplied from the gas source 2 in response to the actuation of the electromagnetic valve 4 to be supplied to the patient through the nose cannula 1.

Next, the operation of the gas feeder to which the thus-arranged synchronization control unit A according to the present invention is applied, is explained below by referring to a timing chart shown in FIG. 5.

As described above, while the electromagnetic valve 4 is kept inoperative, the communication between the nose cannula 1 and the detector 3 is established so that the change in pressure acting upon the nose cannula 1 in response to the inhalation and the expiration can be detected by the detector 3. The electric signals generated from the detector 3 is amplified by the amplifier circuit 5 and then supplied to the control section 6.

The electrical signals 9 from the amplifier circuit 5 are supplied to the comparator 6a to determine whether or not the level of the respective electric signals reach a predetermined voltage level 10. If the electric signal 9 reaches the predetermined voltage level, the comparator 6a generates a signal 11 irrespective of ambient conditions. When the signal 11 is supplied to the logic circuit 6d, a trigger signal 12 is generated from the logic circuit 6d and then supplied to the output circuit 6b.

When the trigger signal 12 is input to the output circuit 6b, an actuation signal 13 is generated from the output circuit 6b for a predetermined period of time and supplied to the electromagnetic valve 4. Upon receipt of the actuation signal 13, the respective ports of the electromagnetic valve 4 are changed over such that the communication between the IN port 4a and the EX port 4c is established to supply oxygen from the gas source 2 to the nose cannula 1 and simultaneously the communication between the IN port 4a and the OUT port 4b is cut off so as not to introduce the pressure of oxygen supplied, in the detector 3.

When the electromagnetic valve 4 returns to its initial state, the pressure of oxygen remaining in the nose cannula 1 is introduced into the detector 3. At this time, there is a likelihood that the pressure of the residual oxygen in the nose cannula 1 is detected by the detector 3 and the electric signals generated from the detector 3 have a level similar to those generated upon the inhalation. In order to prevent the afore-mentioned problem, the mask signal generator circuit 6c generates a mask signal 14 for approximately 0.5 second, using the transition of the actuation signal 13 into a low level as a trigger. The mask signal 14 is supplied to a logic circuit 6d so as not to generate the trigger signal 12 even if the signal 11 is generated from the comparator 6a while the mask signal 14 is generated.

FIG. 6 shows a view for evaluating the performance of the afore-mentioned synchronization control unit A when applied to the breath simulating apparatus not shown. The breath simulating apparatus functions to conduct gas absorption and gas discharge relative to the nose cannula 1 in an amount of 0.16 cc per one absorbing or discharging operation so as to simulate the inhalation and the expiration. The amount of the gas absorbed or discharged by the breath simulating apparatus produces a smaller change in air pressure as compared to those generated by an actual breath of ordinary person.

As is apparent from FIG. 6, the synchronization control unit A according to the present invention, can supply a predetermined amount of gas (oxygen) in synchronization with the timing of the inhalation of the breath simulating apparatus.

Incidentally, the durability of the synchronization control unit A was tested by instantaneously applying the pressure change on the order of 1000 kPa to the detector 3 of the synchronization control unit A from the side of the tube 8. As a result, it was recognized that such a pressure change did not cause any damage or breakage of the synchronization control unit A. The pressure change is considerably larger than those generated upon such a misuse that the nose cannula 1 is erroneously held in the mouth of the patient. Accordingly, the synchronization control unit A according to the present invention has a sufficient durability against instantaneous pressure change generated upon the misuse which is apt to occur in daily experience.

In addition, the expiration of the patient is transmitted to the detector 3 through the nose cannula 1, the electromagnetic valve 4 and the tube 8. In this case, since an interior of each of the afore-mentioned respective members is usually filled with dry oxygen upon ordinary use, the pressure change due to the expiration is propagated through oxygen filled. For this reason, the piezoelectric element 3a can be prevented from being directly exposed to the expiration of the patient. Accordingly, there arises no risk that the piezoelectric element 3a is exposed to a moisture in the expiration and therefore no damage to the performance thereof occurs during the use.

In the afore-mentioned preferred embodiments, explanation is made with respect to the case where the synchronization control unit A is applied to the gas feeder for supplying oxygen to the patient. However, the present invention is not limited to these preferred embodiments. For example, the synchronization control unit A according to the present invention can also be applied to gas feeders used for diving works or high altitude works.

INDUSTRIAL APPLICABILITY

As described in detail hereinbefore, in the synchronization control unit according to the present invention, the inhalation and the expiration act upon a surface of the piezoelectric element constituting the detector in the direction parallel therewith, while the outside air is introduced so as to act upon the surface of the piezoelectric element in the direction opposed thereto, so that it becomes possible to clearly distinguish the inhalation and the expiration from each other. Therefore, by identifying the inhalation by the electric signals generated from the detector to actuate the electromagnetic valve, it is possible to supply a gas only upon the inhalation.

Further, even though a large pressure change occurs on a side of a gas passage due to misuse or the like, the air flow due to such a pressure change is permitted to occur along the surface of the piezoelectric element but prevented from acting upon the surface of the piezoelectric element in the direction perpendicular thereto. Therefore, it is possible to impart a high durability to the synchronization control unit.

Furthermore, when applied to a nose cannula, the synchronization control unit according to the present invention can be used together with commercially available nose cannulae, thereby advantageously providing inexpensive medical apparatuses or the like.

What is claimed is:

1. A breath-synchronization control unit for a gas feeder for supplying a gas from a source to a human in synchronization with breathing, comprising a breath detecting sensor, wherein said breath detecting sensor comprises:

a plate shaped piezoelectric element;

a container having a single space to house said piezoelectric element, an air vent hole connected to outside of the container and disposed so at to face a plane of said plate shaped piezoelectric element, and a breath vent hole for human breathing disposed parallel to the plate shaped piezoelectric element; and a control section which opens and closes a valve of a gas source to supply gas for a predetermined time when said piezoelectric element of said breath detecting sensor detects an inhalation attempt by sensing air pressure from said air vent hole.

2. A breath detecting sensor, comprising:

a plate shaped piezoelectric element for detecting inhalation; and a container having an internal single space housing said plate shaped piezoelectric element, an air vent hole connecting to outside of said container and disposed so as to face a plane of the plate shaped piezoelectric element, and a breath vent hole adapted to be connected to a human body for communicating an inhalation by a human to the plate shaped piezoelectric element disposed parallel to the plane of the plate shaped piezoelectric element.

* * * * *